(12) United States Patent
Narasimhan

(10) Patent No.: US 12,144,654 B2
(45) Date of Patent: Nov. 19, 2024

(54) METHOD OF DETERMINING FUSED SENSOR MEASUREMENT AND VEHICLE SAFETY SYSTEM USING THE FUSED SENSOR MEASUREMENT

(71) Applicant: Continental Automotive GmbH, Hannover (DE)

(72) Inventor: Sreelakshmi Rugmini Narasimhan, Bangalore (IN)

(73) Assignee: Continental Automotive GmbH, Hannover (DE)

(*) Notice: Subject to any disclaimer, the term of this patent is extended or adjusted under 35 U.S.C. 154(b) by 223 days.

(21) Appl. No.: 17/756,566

(22) PCT Filed: Nov. 27, 2020

(86) PCT No.: PCT/EP2020/083561
§ 371 (c)(1),
(2) Date: May 27, 2022

(87) PCT Pub. No.: WO2021/105314
PCT Pub. Date: Jun. 3, 2021

(65) Prior Publication Data
US 2023/0000441 A1    Jan. 5, 2023

(30) Foreign Application Priority Data
Nov. 27, 2019    (GB) ..................... 1917230

(51) Int. Cl.
*A61B 5/00*    (2006.01)
*A61B 5/08*    (2006.01)
(Continued)

(52) U.S. Cl.
CPC .......... *A61B 5/7221* (2013.01); *A61B 5/0816* (2013.01); *A61B 5/364* (2021.01);
(Continued)

(58) Field of Classification Search
CPC ..... A61B 5/7221; A61B 5/0816; A61B 5/364; A61B 5/6893; A61B 5/725;
(Continued)

(56) References Cited

U.S. PATENT DOCUMENTS

| 5,626,140 A | 5/1997 | Feldman et al. |
| 6,313,749 B1 * | 11/2001 | Horne .................... G08B 21/06 340/576 |

(Continued)

FOREIGN PATENT DOCUMENTS

| DE | 102011107241 A1 | 3/2012 |
| DE | 102018103396 A1 | 8/2019 |

(Continued)

OTHER PUBLICATIONS

Intellectual Property Office Search Report dated May 21, 2020 for the counterpart Great Britain Application No. GB1917230.3.

(Continued)

*Primary Examiner* — Hai H Huynh

(57) ABSTRACT

A method of determining a fused sensor measurement is disclosed including: obtaining sensor measurements from sensors detecting a same type of physiological measurement; determining a signal quality index (SQI) of each sensor including determining an extent to which a sensor measurement differs from others among the sensor measurements obtained from each sensor; determining a weightage of each sensor based on the SQI of each sensor; and determining a fused sensor measurement from the plurality of sensors based on the weightage of each sensor and filtered sensor measurements of each sensor obtained from a Kalman filter operation. A vehicle safety system includes: a vehicle electronic control unit configured to: determine the sensor measurement extent, to determine the SQI of each sensor, determine the weightage of each sensor, determine the fused sensor measurement, determine the occupant's (Continued)

physiological condition, and if the physiological condition is abnormal, perform at least one vehicle operation.

18 Claims, 1 Drawing Sheet

(51) Int. Cl.
*A61B 5/364* (2021.01)
*B60R 21/01* (2006.01)

(52) U.S. Cl.
CPC ............ *A61B 5/6893* (2013.01); *A61B 5/725* (2013.01); *A61B 2503/22* (2013.01); *A61B 2562/04* (2013.01); *B60R 21/01* (2013.01)

(58) Field of Classification Search
CPC ..... A61B 5/02405; A61B 5/024; A61B 5/361; A61B 5/363; A61B 5/02; A61B 5/0205; A61B 2562/04; B60R 21/01; B60W 40/08; B60W 2040/0872
USPC .................................. 701/45, 46, 47, 48, 49
See application file for complete search history.

(56) References Cited

U.S. PATENT DOCUMENTS

| | | | |
|---|---|---|---|
| 6,337,629 B1 * | 1/2002 | Bader .................... | G08B 21/06 340/576 |
| 6,575,902 B1 * | 6/2003 | Burton .................. | B60W 40/08 600/595 |
| 7,088,250 B2 * | 8/2006 | Yasushi ................... | A61B 5/18 340/576 |
| 9,622,708 B2 * | 4/2017 | Fujita ................... | A61B 5/0245 |
| 9,815,384 B2 * | 11/2017 | Sugiyama .............. | B60K 28/00 |
| 9,988,055 B1 | 6/2018 | O'Flaherty | |
| 2002/0121981 A1 | 9/2002 | Munch | |
| 2009/0284378 A1 | 11/2009 | Ferren | |
| 2012/0197138 A1 | 8/2012 | Vrazic et al. | |
| 2013/0231582 A1 | 9/2013 | Prasad | |
| 2013/0261477 A1 | 10/2013 | Fuwamoto et al. | |
| 2014/0221781 A1 | 8/2014 | Schrauf et al. | |
| 2015/0025394 A1 | 1/2015 | Hong et al. | |
| 2016/0007935 A1 | 1/2016 | Hernandez et al. | |
| 2017/0181677 A1 | 6/2017 | Varsavsky et al. | |
| 2018/0251122 A1 | 9/2018 | Golston et al. | |
| 2018/0348759 A1 | 12/2018 | Freeman et al. | |
| 2019/0300002 A1 | 10/2019 | Fung et al. | |

FOREIGN PATENT DOCUMENTS

| | | |
|---|---|---|
| EP | 0713675 A2 | 5/1996 |
| WO | 2015138416 A1 | 9/2015 |
| WO | 2015175435 A1 | 11/2015 |
| WO | 2019118060 A1 | 6/2019 |

OTHER PUBLICATIONS

The International Search Report and the Written Opinion of the International Searching Authority mailed on Mar. 5, 2021 for the counterpart PCT Application No. PCT/EP2020/083561.
Paola Pierlenoni, et al., "An Android-Based Heart Monitoring System for the Elderly and for Patients with Heart Disease", International Journal of Telemedicine and Applications, vol. 2014, Article ID 625156, 11 pages, Hindawi Publishing Corporation.
Heathwise Staff, "Heart Rhythm Problems and Driving", Healthwise Inc., Jul. 22, 2018.
MG Tsipouras, et al., "Arrhythmia Classification using the RR-Interval Duration Signal", Computers in Cardiology 2002, vol. 29, pp. 485-488, doi: 10.1109/CIC.2002.1166815.
MG Tsipouras, et al., "An arrhythmia classification system based on the RR-interval signal", Artificial Intelligence in Medicine, 2005, vol. 33, pp. 237-250.
A. Koening, et al., "Statistical sensor fusion of ECG data using automotive-grade sensors", Advances in Radio Science, Nov. 13, 2015, vol. 13, pp. 197-202, Copernicus Publications, Deutschaland, doi: 10.5194/ars-13-197-2015.
Notice of Reasons for Refusal drafted Apr. 12, 2023 for the counterpart Japanese Patent Application No. 2022-522730 and Global Dossier Translation.
European Examination Report dated Aug. 1, 2024 for the counterpart European Patent No. 20 816 436.8 and machine translation of same.
Li Q et al: "Robust heart rate estimation from multiple asynchronous noisy sources using signal quality indices and a Kalman filter"; Physiological Measurement, Institute of Physics Publishing, Bristol, GB, vol. 29, No. 1, Jan. 1, 2008 (Jan. 1, 2008), pp. 15-32, XP020130214, ISSN: 0967-3334. Cited in NPL Cite No. 1.

* cited by examiner

METHOD OF DETERMINING FUSED SENSOR MEASUREMENT AND VEHICLE SAFETY SYSTEM USING THE FUSED SENSOR MEASUREMENT

FIELD OF INVENTION

The invention relates to a method of determining a fused sensor measurement and a vehicle safety system using the fused sensor measurement.

BACKGROUND OF INVENTION

To combat accidents caused by drowsiness and fatigue of drivers, systems have been developed to monitor and analyse the drivers' biological signals from cardiovascular activity, brain activity, respiratory activity, eye lid closure, etc. Together with analysis of vehicle behaviour, such as variations in steering wheel movement, position of vehicle and velocities, the vehicle's occupants or other interested parties may be alerted or notified of driver fatigue. Comfort functions or driver assistance systems may also be activated in response to driver fatigue.

However, such developments often overlook drivers' medical conditions, which can inhibit driving ability and contribute to traffic accidents. Studies have shown that a small but significant percentage of collisions involving casualties had the driver's medical conditions as a main factor, with cardiac-related events contributing to such collisions. Hence, the health of a driver must be addressed to increase safety while driving.

There are many known systems that analyse the health of a driver during driving. Some systems use different types of health data to identify a medical condition that the driver may be experiencing. However, such systems may involve complex algorithms. The known systems may not be economical or may suffer from processing latency as a result.

There is therefore a need to provide an alternative method of using health data to increase the safety of operating vehicles.

SUMMARY

It is therefore an object to provide a method of using sensor data and a vehicle safety system to address the problems discussed above.

To accomplish this and other objects, there is provided, in an aspect, a method of determining a fused sensor measurement, the method including: obtaining, by a processor, a number of sensor measurements from each of a plurality of sensors detecting a same type of physiological measurement; determining, by the processor, a signal quality index of each sensor, wherein the signal quality index includes determining an extent to which a sensor measurement differs from the others among the number of sensor measurements obtained from each sensor; determining, by the processor, a weightage of each sensor based on the signal quality index of each sensor; and determining, by the processor, a fused sensor measurement from the plurality of sensors based on the weightage of each sensor and filtered sensor measurements of each sensor obtained from a Kalman filter operation.

In another aspect, there is provided a vehicle safety system including: a plurality of sensors detecting a same type of physiological sensor measurement from an occupant in the vehicle; and a vehicle electronic control unit including at least one processor. The at least one processor is configured to: obtain the sensor measurements from the plurality of sensors, determine an extent to which a sensor measurement differs from the others among the number of sensor measurements obtained from each sensor, to determine a signal quality index of each sensor, determine a weightage of each sensor based on the signal quality index of each sensor, determine a fused sensor measurement from the plurality of sensors based on the weightage of each sensor and filtered sensor measurements of each sensor obtained from a Kalman filter operation, determine a physiological condition of the occupant based on the fused sensor measurement, and if the physiological condition is abnormal, perform at least one vehicle operation in response to the abnormal physiological condition.

The present disclosure may be useful for fusing data from any type of sensor. In an implementation, a suitable sensor may be one that detects physiological data. The sensor may detect physiological data of any subject. The sensor may detect physiological data of a human subject. In an implementation, the sensors may detect physiological data of an occupant in a vehicle.

The present disclosure takes into account the extent to which measurements from a sensor differ from each other. Measurement data points in a data set that are less spread out indicates a lower extent that measurements from a sensor differ from each other. A sensor that provides consecutive measurement data points that are less spread out may suggest that the sensor provides a more dependable data set, and therefore may be assigned a higher weightage. Furthermore, noise picked up at the time the sensor detects a sensor measurement may cause the sensor measurement to vary from the other measurements in the data set to a larger extent. Thus, a sensor that provides noisy or incoherent data may be assigned a lower or zero weightage. A sensor measurement that is incoherent or that differs by a large extent from an average may be assigned a lower or zero weightage. An inconsistent sensor measurement may advantageously be identified at the time of receipt from the sensor. Such sensor measurement may advantageously be assigned a lower or zero weightage in the determination of a fused sensor measurement. Identification of an unreliable sensor measurement aids in reducing any unnecessary processing involved in calculation of a fused sensor measurement. Advantageously, processing of the fused sensor measurement may be optimized and may not suffer from processing latency.

The signal quality index of a sensor refers to the quality of a signal transmitted by the sensor. The quality of the signal may refer to the quality of a measurement detected by the sensor. The signal quality index may be determined by the disclosed processor or by the sensor. The signal quality index of a sensor may be determined, in part, by determining the extent to which measurements from a sensor differ from each other. The signal quality index of a sensor may include other factors. The signal quality index of a sensor may be determined, in part, by determining a difference between a sensor measurement and its previous sensor measurement. The difference between consecutive measurements provides an indication of whether the change in the measurements is natural. The signal quality index of a sensor may be determined, in part, by comparing the measurement itself against realistic measurements. Subsequent steps of processing a sensor measurement may advantageously be based on the signal quality index of the sensor. The signal quality index of the sensor may advantageously be used to modify an operation to filter the sensor measurements. The signal quality index of a sensor may advantageously be used to modify the weightage of the sensor. The signal quality index of a sensor may advantageously be used to modify the calculation of the fused sensor measurement from all sensors. The present disclosure is therefore advantageously suitable for determining an appropriate data point from multiple sensors providing multiple data points. The fused sensor measurement obtained according to the present disclosure may reflect a more accurate measurement of the physiological data detected by the multiple sensors.

The signal quality index of a sensor may be determined on a single type of physiological data, for example heart rate of an occupant in a vehicle, or in another example the respiratory rate of the vehicle occupant. The single type of physiological data may be processed according to the present disclosure, to obtain a more accurate measurement of that data type. Advantageously, a more accurate fused measurement of the chosen data type may be obtained. Further advantageously, because one type of data is processed, the time taken to obtain the fused sensor measurement may be lesser.

Sensors may be configured to detect one or more than one type of physiological data. Where more than one type of data is detected or obtained, each type of data may be processed according to the present disclosure.

A number of sensor measurements obtained from each sensor may form a data set for processing by the processor. The number of sensor measurements in a data set may be selected to be sufficient for determining the signal quality index of a sensor. The larger the number of sensor measurements, the extent to which each sensor measurement differs from the other may be better determined. It has been found that using a number of sensor measurements from each sensor provides better results of fused measurements, than fused measurements derived from a single data point from each sensor. The extent or the spread may refer to how much a measurement differs from an average measurement derived from the number of sensor measurements. The extent to which each sensor measurement differs from the other may be determined by mathematical operations. The extent to which each sensor measurement differs from the other may be determined by a variance or variability of the sensor measurements from the arithmetic mean of the sensor measurements. The extent to which each sensor measurement differs from the other may be determined by a standard deviation of the data set. The extent to which each sensor measurement differs from the other may be determined by other suitable mathematical operations, including but not limited to skewness, kurtosis and root mean square operations. The signal quality index may include a variance operation of the number of sensor measurements obtained from each sensor. The signal quality index may include a standard deviation operation of the number of sensor measurements obtained from each sensor. The signal quality index may include other suitable mathematical operations, including but not limited to skewness, kurtosis and root mean square operations, of the number of sensor measurements obtained from each sensor. The minimum number of sensor measurements sufficient for determining the signal quality index (SQI) of a sensor may be appropriately determined. The minimum number of sensor measurements sufficient for determining the signal quality index (SQI) of a sensor may be dependent on various factors. Exemplary factors include the type of SQI being determined, the type of physiological measurement for which the SQI is being calculated, and the sampling frequency of the sensor (number of data points per second sampled by the sensor). The present disclosure advantageously uses number of sensor measurements or samples or data points, instead of a predetermined time window to obtain a data point, because different physiological data may have different time periods where a change in value may occur. Having shorter time windows may be inefficient. Optimizing the time window to fit constantly variable data points, e.g. physiological data, may unnecessarily consume processing power. Advantageously, the present disclosure proposes to use the sensor measurement(s) itself to determine the signal quality index of the sensor. Using number of sensor measurements allows the signal quality index to be independent of the time factor. Specifically, the present disclosure advantageously uses an extent to which a measurement differs from other measurements in its data set to, in part, determine the quality of measurements received from the sensor. A sensor that outputs quality measurements may advantageously have a higher weightage in the calculation of a fused sensor measurement. Further advantageously, the present disclosure provides the use of sensor measurement(s) or physiological measurement(s) in determining signal quality of the multiple sensors and/or determining weightage of the multiple sensors, instead of using parameters of the sensor or electrode itself. The use of sensor measurement(s) or physiological measurement(s) may reduce the time taken to detect an abnormal physiological condition. The vehicle may advantageously react faster to any abnormal physiological condition detected. Yet further advantageously, the use of sensor measurement(s) or physiological measurement(s), instead of parameters of the sensor or electrode itself, permits easier incorporation of plug-and-play devices, for example, devices worn by the vehicle occupant.

The fused sensor measurement may be used as input in the determination of a physiological condition of the subject. Advantageously, the use of a plurality of sensors to obtain a single reliable output at each time point may increase the reliability of the disclosed vehicle safety system to detect physiological conditions.

Advantageously, the disclosed vehicle safety system may be able to detect an abnormal physiological condition more accurately. Advantageously, the disclosed vehicle safety system may be able to instruct or perform one or more appropriate vehicle operations in good time to respond to the abnormal physiological condition.

DETAILED DESCRIPTION

Figure 1:
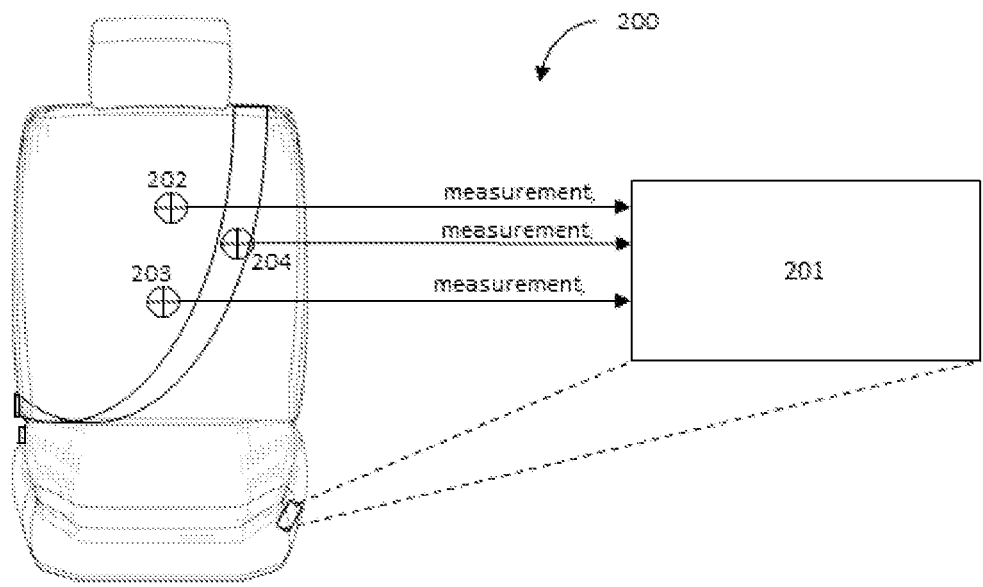
FIG. 1 shows an illustration of a vehicle safety system 200 including sensors 202, 203 and 204 and vehicle seat electronic control unit (ECU) 201 according to an embodiment of the present disclosure.

Hereinafter, exemplary embodiments of the present invention will be described in detail with reference to the accompanying drawings. The detailed description of this invention will be provided for the purpose of explaining the principles of the invention and its practical application, thereby enabling a person skilled in the art to understand the invention for various exemplary embodiments and with various modifications as are suited to the particular use contemplated. The detailed description is not intended to be exhaustive or to limit the invention to the precise embodiments disclosed. Modifications and equivalents will be apparent to practitioners skilled in this art and are encompassed within the spirit and scope of the appended claims.

In an embodiment, there is provided a method of determining a fused sensor measurement. The method includes obtaining, by a processor, a number of sensor measurements from each of a plurality of sensors detecting a same type of physiological measurement. The method further includes determining, by the processor, a signal quality index of each sensor, wherein the signal quality index includes determining an extent to which a sensor measurement differs from the others among the number of sensor measurements obtained from each sensor. The method further includes determining, by the processor, a weightage of each sensor based on the signal quality index of each sensor. The method further includes determining, by the processor, a fused sensor measurement from the plurality of sensors based on the weightage of each sensor and filtered sensor measurements of each sensor obtained from a Kalman filter operation.

In another embodiment, there is provided a vehicle safety system. The vehicle safety system includes a plurality of sensors detecting a same type of physiological sensor measurement from an occupant in the vehicle. The vehicle safety system further includes a vehicle electronic control unit having at least one processor. The at least one processor is configured to obtain the sensor measurements from the plurality of sensors. The at least one processor is configured to determine an extent to which a sensor measurement differs from the others among the number of sensor measurements obtained from each sensor, to determine a signal quality index of each sensor. The at least one processor is configured to determine a weightage of each sensor based on the signal quality index of each sensor. The at least one processor is configured to determine a fused sensor measurement from the plurality of sensors based on the weightage of each sensor and filtered sensor measurements of each sensor obtained from a Kalman filter operation. The at least one processor is configured to determine a physiological condition of the occupant based on the fused sensor measurement. If the physiological condition is abnormal, the at least one processor is configured to perform at least one vehicle operation in response to the abnormal physiological condition.

The plurality of sensors may detect the physiological measurement from an occupant in a vehicle. The plurality of sensors may be arranged such that physiological measurements can be obtained from the vehicle occupant. The plurality of sensors may be located in the vehicle cabin. One or some or all of the sensors may be part of the vehicle. One or some or all of the sensors may be consumer devices or aftermarket devices that can be used to obtain physiological measurements from the vehicle occupant. For sensors that require contact of the vehicle occupant in order to obtain a sensor measurement, the sensor may be arranged in such suitable location. For example, a sensor may be arranged in a vehicle seat or embedded within the vehicle seat. A sensor may be arranged on a seatbelt or a steering wheel or any other suitable location. A sensor may be part of a device worn by the vehicle occupant, for example a wearable device that can obtain physiological measurements. Other types of sensors may require a line of sight to the vehicle occupant in order to obtain a sensor measurement. Such sensors may be located suitably. The plurality of sensors may be a combination of any type of sensor that can detect the physiological measurement from the vehicle occupant. In an implementation, the plurality of sensors is arranged in a vehicle seat, a seatbelt, a wearable device, or combinations thereof.

A type of physiological measurement useful to increase safety of a vehicle may be heart rate of the vehicle occupant. As mentioned above, cardiac-related events contribute to traffic casualties. Particularly, heart arrhythmia or arrhythmia is a common abnormality that can be detected to improve road safety. Arrhythmias are improper irregular beats of the heart. Arrhythmia occurs when the electrical impulses that coordinate the heartbeats malfunction. Some heart arrhythmias such as heart flutter or a racing heartbeat may be harmless, but some arrhythmias may be life-threatening.

Arrhythmias that most people experience include bigeminy and trigeminy. Bigeminy and trigeminy are patterns of normal heartbeats alternating with premature heartbeats that occur just before a normal heartbeat. A person experiencing bigeminy or trigeminy may feel heart flutter or like the heart is skipping a beat or may feel chest pain or shortness of breath. Bigeminy and trigeminy usually occur without any significant symptoms and is typically not a cause for concern. However, the premature heartbeats or premature ventricular contractions (PVC) may indicate an impending serious problem. Persons that experience PVC may, with time, risk developing more serious arrhythmias like ventricular fibrillation, which can lead to blood clot which may cause stroke if the clot travels to the brain. Additional workload on the heart due to the additional premature heartbeats may lead to heart enlargement and possibly heart failure in the future. It may be useful to monitor the occurrences of bigeminy or trigeminy for medical baselining or other health-related services.

Arrhythmias manifesting as a faster heart rate is termed tachycardia. Persons that experience tachycardia may feel chest pain or shortness of breath. Arrhythmias manifesting as a slower heart rate is termed bradycardia. Persons that experience bradycardia may feel dizziness. It may be useful to monitor for such occurrences in case vehicle operation is impaired.

The heart beating at a high rate for a prolonged period of time can be lethal. Particularly, ventricular tachycardia occurs when the lower chambers of the heart beat at a high rate for a prolonged period of time. For example, it can be lethal if a heart rate goes beyond a rate threshold of 150 bpm for a duration threshold of more than 30 seconds. The detection of ventricular tachycardia is critical in order to ensure safety or corrective actions of the vehicle are done.

A heart that beats erratically and at an even higher rate is lethal. The heart may stop abruptly as a result. Ventricular fibrillation occurs when the lower chambers of the heart beat at a very high rate in an uncoordinated manner. Ventricular fibrillation may occur when the heart rate goes beyond a rate threshold of 250 bpm. Ventricular fibrillation is the most frequent cause of sudden cardiac deaths. Thus, the detection of ventricular fibrillation is critical in order to ensure safety or corrective actions of the vehicle are done as soon as possible.

Heart rate or heartbeats may be used to detect arrhythmias. Some sensors detect heart rate by detecting the pulse or by detecting an electric signal of the heartbeat. Some sensors detect heart rate by detecting and measuring blood flow through the skin. Some sensors detect heart rate by detecting colour changes of the skin. Some sensors detect heart rate by measuring an amount of light that reflects back from the skin. In the automotive environment, galvanic or capacitive sensors may be built into the steering wheel, in the seat or seatbelt. Seismocardiography, photoplethysmography or impedance cardiography may alternatively be used.

Heart rate variability (HRV) is the variation in the time interval between consecutive heartbeats. HRV may be used because there is constant variation in time between heartbeats of a normal, healthy heart. HRV may increase during relaxing activities and may decrease during periods of stress. Therefore, HRV may be useful to interpret an emotional state of a person or a vehicle occupant. Broadly, HRV measures the specific changes in time (typically seconds or milliseconds) between consecutive heartbeats, while heart rate provides an average number of heartbeats per minute. There are different methods to calculate HRV. Sensors detecting heart rate may calculate HRV values from the detected heart rate values using any method. Where HRV values are selected as the sensor measurement to be obtained from the plurality of sensors, the sensors may be configured to output the HRV values.

Respiratory rate may also be used to detect arrhythmias. Respiratory rate may be used in conjunction with heart rate to detect arrhythmias. The use of respiratory rate and heart rate may provide a more comprehensive evaluation of cardiopulmonary activity. Therefore, respiratory rate may also be a type of physiological measurement useful to increase safety of a vehicle. Respiratory rate may be detected by different methods, which is not in the scope of this disclosure.

Sensor measurements may be periodically obtained. Sensor measurements may be periodically obtained by the processor from the sensor. The periodic time interval may be predefined. At each time interval, a sensor measurement may be obtained from each sensor. The time interval at which each of the plurality of sensors outputs a measurement or a data point may be synchronized between the plurality of sensors. A data point may be obtained from each sensor at about the same time. A data point may be obtained at each predefined time interval from every sensor.

A Kalman filter operation may be performed on each sensor measurement obtained from the sensors. The sensor may be configured to perform the Kalman filter operation. The disclosed processor may be configured to perform the Kalman filter operation. The step of performing the Kalman filter operation may be performed before or after the determination of the signal quality index.

A sensor measurement obtained from each sensor may form a group of sensor measurements that can be fused. A filtered sensor measurement obtained from each sensor may form a group of measurements that can be fused. The fused sensor measurement may take into account the Kalman filtered measurement. The fused sensor measurement may represent an average measurement detected across the plurality of sensors at a time point. The fused sensor measurement may represent a mathematical operation of an average measurement detected across the plurality of sensors at a time point. For example, the fusion of the sensor measurements may consider an extent to which a sensor measurement differs from sensor measurements of the other sensors in the group. A sensor measurement that is far away from the average is given a lower weightage in the fused sensor measurement, while a sensor measurement that is close to the average is given a higher weightage in the fused sensor measurement.

In an embodiment, a sensor measurement obtained from each sensor may be processed together with one or more other sensor measurements from the sensor, to determine whether the sensor measurement should be included in the fusion or not. If a filter operation or any other type of evaluation determines that the sensor measurement is not from a reliable signal, the sensor measurement may not be included in the subsequent steps. Advantageously, evaluating a sensor measurement against consecutive measurements according to the present disclosure complements filter operations, e.g. a Kalman filter operation, that are typically used with sensor fusion. As mentioned above, the signal quality index of a sensor may be used to modify filter operations.

Sensor measurements from a number of time intervals may be obtained for each sensor. The number of sensor measurements obtained from each sensor may be sufficient to determine the signal quality index of the sensor. Therefore, the signal quality index of the sensor may be determined at least only after the first sensor measurement from the sensor is obtained. A measurement from a sensor and its next few measurements may be used to form a group or a data set of sensor measurements from that sensor. Where there are sufficient past measurements to form the group or data set, a measurement from the sensor and its past few measurements may be used for that sensor. Each measurement may or may not be filtered. The extent to which a sensor measurement differs from the others in the group or data set of sensor measurements from a sensor may then be evaluated to determine the signal quality index of the sensor. The signal quality index of the sensor may be determined by determining a variance operation or standard deviation operation of the sensor measurement in question against the group of sensor measurements obtained from that sensor. The variance or standard deviation may be obtained for the sensor measurement in question. A higher variance or standard deviation indicates a lower signal quality index of that sensor.

In an embodiment, the variance may be represented as:

$$\text{variance} = \frac{\sum_{i=1}^{n}(x_i - \mu)^2}{n}$$

where n is the number of sensor measurements (sample size) obtained from each sensor at a time point; x is the value of the current sensor measurement i; and $\mu$ is the arithmetic mean of the values of the sample size.

The extent to which a sensor measurement differs from the other may be compared against known thresholds or known values of such extent, in order to determine whether the measurements from that sensor should be considered or not. If the extent or the variance or the standard deviation exceeds the threshold, the current measurement i from that sensor may be ignored or may be given a lower or zero weightage. If the extent or the variance or the standard deviation is within the threshold, the current measurement i from that sensor may be given a higher weightage. The weightage of the measurement i or the weightage of the sensor may be included in the calculation of the fused sensor measurement. Alternatively, a measurement i, of which its extent or variance or standard deviation exceeds a first threshold but is within a second threshold, may be included in the fusion, but at a lower weightage, and a measurement j of which its extent or variance or standard deviation exceeds the second threshold may be ignored or given a zero weightage.

The weightage of each sensor may be based on the signal quality index of the sensor. The weightage may also consider the filtered sensor measurements of each sensor. The filtered sensor measurements may be obtained from a Kalman filter operation. A measurement i obtained from a sensor that is to be included in the fusion may undergo a Kalman filter operation, which may be considered in determining the weightage of a sensor. In an embodiment, the weightage may be represented as $$\frac{|\text{filtered sensor value} - \text{actual sensor value}|}{SQI}.$$

A smaller difference between the filtered measurement and the actual measurement suggests that the sensor provides a more dependable measurement i. As mentioned previously, the signal quality index (SQI) of the sensor suggests that the sensor provides a more dependable measurement i or data set of measurements. Therefore, the weightage may be based on a difference between the filtered measurement and the actual measurement from the sensor as well as the SQI of the sensor. A sensor that provides a dependable measurement i may be assigned a higher weightage. Conversely, a sensor that provides a measurement i that differs from its filtered value past a threshold or differs from an average of its consecutive measurements past a threshold may be assigned a lower weightage. A sensor that provides a measurement i that differs from its filtered value past a threshold and differs from an average of its consecutive measurements past a threshold may be assigned an even lower weightage or a zero weightage. Thus, the weightage calculated for each sensor may represent an actual weightage or relevance of the measurements from each sensor. The weightage may be included in the calculation of the fused sensor measurement.

The measurements i may be input into the fusion calculation. The filtered measurements i of each sensor obtained from a Kalman filter operation may be input into the fusion calculation. Each measurement i may be scaled or multiplied by its weightage or the weightage of its sensor. A measurement i that has a zero weightage may be ignored in the fusion calculation. A measurement i that has a non-zero weightage may be considered in the fusion calculation together with its percent weightage. In an embodiment, the fused value may be a summation of the weightage of each sensor multiplied by the filtered sensor measurement from that sensor.

The fused sensor measurement at time i may be used to determine a physiological condition of the vehicle occupant. Determination of a physiological condition of the occupant based on the fused sensor measurement may include classifying the fused measurement. The fused measurement may be classified into a suitable classification for the particular physiological measurement. Classifying the fused measurement may include comparing the fused measurement based on known thresholds for the particular physiological measurement. Classifying the fused measurement may include analysing the measurement based on known methods. Classifying the fused measurement may include using a mathematical model or machine learning model.

Possible vehicle operations in response to an abnormal physiological condition may be suitably determined. The possible vehicle operations may be taken so as to reduce the impact of a potential accident that may be caused due to a driver who is inflicted with the detected physiological condition. For less critical physiological conditions, suitable vehicle operations may include generating an in-vehicle alarm to alert the vehicle occupant, storing the measurement or detected physiological condition in the processor for monitoring, transmitting the measurement or detected physiological condition to a remote facility for monitoring, activating comfort functions to mitigate the condition, combinations thereof and/or with other possible vehicle operations. For more critical physiological conditions, suitable vehicle operations may include crash-related actions like seat-belt pre-tensioning and airbag preparation, placing a notification or an automated call to a medical facility or emergency services, activating an advanced driving assistance system or automated driving functionality in the vehicle, such as automatic steering to the roadside or to a medical facility, allowing remote operation of the vehicle, alerting neighbouring vehicles, combinations thereof and/or with other possible vehicle operations. Vehicle operations for the less critical conditions may be performed for the more critical condition, as appropriate, and vice versa.

The disclosed processor may be part of a computing device that processes a plurality of sensor data. The computing device may be a vehicle electronic control unit. The disclosed processor may be part of a vehicle electronic control unit. The computing device may include computer-readable storage media or computer-readable memory which may include transitory and non-transitory memory. The computer-readable storage media may encompass any electronic component capable of storing electronic information. The computer-readable storage media or memory may include transitory processor-readable media such as random access memory (RAM) or cache memory. The computer-readable storage media or memory may include non-transitory processor-readable media such as read-only memory (ROM), non-volatile random access memory (NVRAM), programmable read-only memory (PROM), erasable programmable read only memory (EPROM), electrically erasable PROM (EEPROM), flash memory, magnetic or optical data storage, registers, etc. The memory is in electronic communication with the disclosed processor and/or other processors of the computing device. Computer-readable instructions may reside in the non-transitory computer-readable storage medium. Computer-readable instructions may be implemented as a program or a code that can be read by the processor. The disclosed method may be implemented as a program or a code that can be read by the processor. Exemplary processor(s) of the computing device include a central processing unit (CPU), a microprocessor, a digital signal processor (DSP), a controller, a microcontroller, a state machine, programmable gate arrays, systems-on-chip (SoC), programmable SoCs, or other suitable devices. The term "processor" may include a combination of processing devices, e.g., a combination of a DSP and a microprocessor, a plurality of microprocessors, one or more microprocessors in conjunction with a DSP core, or any other such configuration suitable for the disclosed system.

Any control unit of the vehicle may be suitable to implement the present disclosure. The control unit may be selected depending on the requirements needed. The control unit may be selected to be in proximity to the implementation of a vehicle operation. For example, the electronic control unit may be an airbag control unit. The airbag control unit may be configured according to the present disclosure. When an abnormal physiological condition is detected, the airbag control unit may trigger an airbag to inflate in response to the abnormal physiological condition. The electronic control unit may be a telematics control unit. The telematics control unit may be configured according to the present disclosure. When an abnormal physiological condition is detected, the telematics control unit may transmit a wireless signal to a remote facility or individual or entity. The control unit may be selected to be in proximity to the plurality of sensors. The electronic control unit may be a computing device that receives measurements from sensors in the vehicle or driver monitoring sensors in the vehicle or physiological sensors in the vehicle. Such control unit may receive and process the sensor measurements according to the present disclosure. Such control unit may transmit the processed data to other control units in the vehicle. The electronic control unit may be a vehicle central computer. The electronic control unit may be a vehicle seat control unit.

Figure 2:
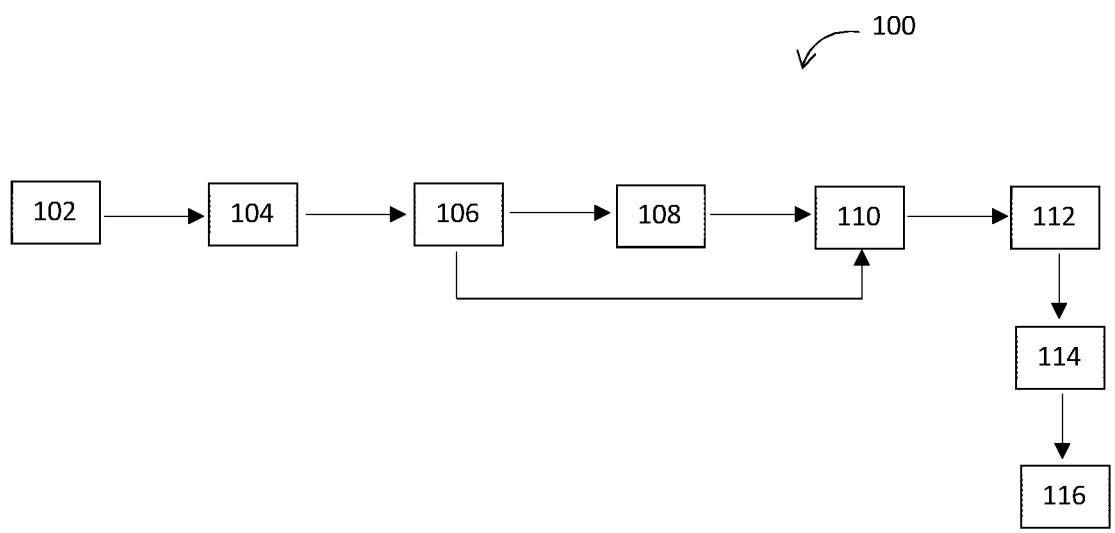
FIG. 2 shows a flowchart of a method 100 of determining a fused sensor measurement performed in ECU 201 according to an embodiment of the present disclosure.

An illustration of a vehicle safety system 200 including sensors 202, 203 and 204 and vehicle seat electronic control unit (ECU) 201 is shown in FIG. 1. A flowchart of method 100 of determining a fused sensor measurement according to an embodiment of the present disclosure performed in ECU 201 is shown in FIG. 2.

A heart rate measurement at time i is obtained from each of three sensors, two built into the vehicle seat and one arranged on the seatbelt. The three heart rate measurements at time i are transmitted to a processor of the vehicle seat electronic control unit (ECU) 201. In ECU 201, the method 100 is performed. In step 102, ECU 201 obtains measurement$_i$ from sensor 202 as well as the measurements for the past four time intervals (measurement$_{i-1}$, measurement$_{i-2}$, measurement$_{i-3}$ and measurement$_{i-4}$) for determining the quality of the measurements from sensor 202. The same is done for sensor 203 and 204. It has been found that using five sensor measurements provides optimal results in the determination of a fused sensor measurement. Further advantageously, the use of five samples applies to any type of data to be fused, including heart rate, heart rate variability and respiratory rate. Furthermore, using number of measurements, as opposed to using a predetermined time window, allows the fusion to be independent of the data that is fused. Consider a 0.5 second time interval chosen for obtaining heart rate measurements, which is below the normal interval between heartbeats. Since changes in heart rate measurement may not occur every 0.5 seconds, the 0.5 second window may not be efficient. Optimizing a time window to obtain variable data, such as physiological data, may be difficult. Thus, using number of sensor measurements allows the signal quality index to be independent of the time factor.

In step 104, the signal quality index of each sensor is determined. To determine the signal quality index, the variance of the five samples from each sensor is determined. The variance is compared against known variance thresholds. If the variance exceeds the threshold, a value of 0 is assigned. If not, a value of 1 is assigned. To determine the signal quality index, the difference between the current sensor measurement$_i$ and the previous sensor measurement$_{i-1}$ is also determined. The difference is compared against a predetermined threshold. If the difference exceeds the threshold, a value of 0 is assigned. If not, a value of 1 is assigned. To determine the signal quality index, the measurement$_i$ is also considered. If measurement$_i$ is below a lower heart rate limit or above an upper heart rate limit, a value of 0 is assigned. If not, a value of 1 is assigned. The assigned values are then added up to determine the signal quality index of that sensor.

In step 106, a Kalman filter operation is performed on every sensor measurement obtained from the sensors.

In step 108, the weightage of each sensor is determined based on the signal quality index of each sensor. The weightage is also based on the difference between the Kalman filtered measurement$_i$ and the actual measurement$_i$.

In step 110, say the measurement$_i$ from sensor 204 is to be ignored in the fusion and the measurements$_i$ from sensors 202 and 203 are to be considered in the fusion, based on a zero weightage of sensor 204 and a 100% weightage of sensors 202 and 203. The fused sensor measurement may be determined by summing the measurement$_i$ scaled by the weightage of the sensors. The fused sensor measurement may be determined by summing the Kalman filtered measurement$_i$ scaled by the weightage of the sensors. Therefore, a zero weightage of sensor 204 means that measurement$_i$ from sensor 204 is ignored or not included in the calculation of the fused sensor measurement.

In step 112, the fused heart rate measurement at time i is classified as a normal heartbeat or a ventricular fibrillation heartbeat or a PVC heartbeat based on known thresholds. Fused heart rate measurements at subsequent time intervals (i+1, i+2, . . . ) are similarly classified accordingly.

In step 114, the classified heartbeats are monitored to determine whether an abnormal physiological condition has developed. A pattern of heartbeats including ventricular fibrillation heartbeat(s) and/or PVC heartbeat(s) may be classified as a heart arrhythmia. An episode of a heart arrhythmia may be classified into a specific type of arrhythmia using methods known in the art.

In step 116, at least one vehicle operation is performed in response to a detected arrhythmia. If it is determined that a bigeminy or trigeminy episode has occurred, the episode is stored in ECU 201 or transmitted to a remote location for storage or to a healthcare practitioner for monitoring. The remote location may be administered by telematics services, healthcare services or hospitals. The stored occurrences of bigeminy or trigeminy may be monitored for development of more serious conditions. If it is determined that a ventricular fibrillation episode has occurred and persists for an appropriate amount of time, e.g. 1 minute, ECU 201 may instruct an advanced driving assistance system to intervene or may transmit a wireless signal to call for immediate medical assistance. An appropriate amount of time to monitor whether a ventricular tachycardia episode persists may be about 3 minutes, and if past the threshold, at least one safety or corrective action may be taken by ECU 201. An appropriate amount of time to monitor whether a tachycardia or bradycardia episode persists may be about 5 to 10 minutes, and if past the threshold, at least one safety or corrective action may be taken by ECU 201.

The invention claimed is:

1. A method of determining a fused sensor measurement, the method comprising:
   a. obtaining, by a processor, a number of sensor measurements from each of a plurality of sensors detecting a same type of physiological measurement;
   b. determining, by the processor, a signal quality index of each sensor, wherein the signal quality index comprises determining an extent to which a sensor measurement differs from others among the number of sensor measurements obtained from each sensor;
   c. determining, by the processor, a weightage of each sensor based on the signal quality index of each sensor and a difference between a filtered sensor measurement and an actual sensor measurement of such sensor;
   d. determining, by the processor, a fused sensor measurement from the plurality of sensors based on the weightage of each sensor and filtered sensor measurements of each sensor obtained from a Kalman filter operation.

2. The method of claim 1, wherein the plurality of sensors detects the physiological measurement from an occupant in a vehicle.

3. The method of claim 1, wherein the plurality of sensors detects a heart rate or a respiratory rate of an occupant in a vehicle.

4. The method of claim 1, wherein the number of sensor measurements obtained from each sensor is sufficient to determine the signal quality index of the sensor.

5. The method of claim 1, wherein the signal quality index comprises a variance operation of the number of sensor measurements obtained from each sensor.

6. The method of claim 1, wherein the plurality of sensors is arranged in a vehicle seat, a seatbelt, a wearable device, or combinations thereof.

7. The method of claim 1, wherein the processor is part of a vehicle electronic control unit.

8. The method of claim 1, further comprising:
determining a physiological condition of the occupant based on the fused sensor measurement, and
if the physiological condition is determined to be abnormal, performing at least one vehicle operation in response to the abnormal physiological condition.

9. The method of claim 1, wherein the filtered sensor measurement used in determining the weightage of each senor and the filtered sensor measurement used in determining the fused sensor measurement are the same.

10. A vehicle safety system comprising:
a plurality of sensors detecting a same type of physiological sensor measurement from an occupant in the vehicle;
a vehicle electronic control unit comprising at least one processor, the at least one processor configured to:
obtain the sensor measurements from the plurality of sensors,
determine an extent to which a sensor measurement differs from others among the number of sensor measurements obtained from each sensor, to determine a signal quality index of each sensor,
determine a weightage of each sensor based on the signal quality index of each sensor and a difference between a filtered sensor measurement and an actual sensor measurement of such sensor,
determine a fused sensor measurement from the plurality of sensors based on the weightage of each sensor and filtered sensor measurements of each sensor obtained from a Kalman filter operation,
determine a physiological condition of the occupant based on the fused sensor measurement, and
if the physiological condition is abnormal, perform at least one vehicle operation in response to the abnormal physiological condition.

11. The system of claim 10, wherein the plurality of sensors detects a heart rate or a respiratory rate of the occupant.

12. The system of claim 10, wherein the abnormal physiological condition is heart arrhythmia.

13. The system of claim 10, wherein the number of sensor measurements obtained from each sensor is sufficient to determine the signal quality index of the sensor.

14. The system of claim 10, wherein the signal quality index comprises a variance operation of the number of sensor measurements obtained from each sensor.

15. The system of claim 10, wherein the plurality of sensors is arranged in a vehicle seat, a seatbelt, or a combination thereof.

16. The system of claim 10, wherein the vehicle electronic control unit is configured to obtain the same type of physiological sensor measurement from a wearable device worn by the occupant.

17. The system of claim 10, wherein the vehicle electronic control unit is a vehicle seat control unit.

18. The vehicle safety system of claim 10, wherein the filtered sensor measurement used in determining the weightage of each senor and the filtered sensor measurement used in determining the fused sensor measurement are the same.

\* \* \* \* \*